(12) United States Patent
Imasugi et al.

(10) Patent No.: US 11,810,659 B2
(45) Date of Patent: Nov. 7, 2023

(54) MEDICAL IMAGE PROCESSING APPARATUS, PROGRAM INSTALLABLE INTO MEDICAL IMAGE PROCESSING APPARATUS, AND MEDICAL IMAGE PROCESSING METHOD

(71) Applicant: CANON KABUSHIKI KAISHA, Tokyo (JP)

(72) Inventors: Yusuke Imasugi, Tokyo (JP); Tsuyoshi Sakamoto, Kitakyushu (JP); Noriaki Miyake, Kitakyushu (JP)

(73) Assignee: Canon Kabushiki Kaisha, Tokyo (JP)

( * ) Notice: Subject to any disclaimer, the term of this patent is extended or adjusted under 35 U.S.C. 154(b) by 131 days.

(21) Appl. No.: 17/227,083

(22) Filed: Apr. 9, 2021

(65) Prior Publication Data

US 2021/0257083 A1 Aug. 19, 2021

Related U.S. Application Data

(63) Continuation of application No. 15/965,159, filed on Apr. 27, 2018, now Pat. No. 10,984,906, which is a
(Continued)

(30) Foreign Application Priority Data

| Oct. 29, 2015 | (JP) | 2015-213477 |
| Oct. 29, 2015 | (JP) | 2015-213478 |
| Oct. 29, 2015 | (JP) | 2015-213479 |

(51) Int. Cl.
*G16H 30/20* (2018.01)
*G06T 17/00* (2006.01)
(Continued)

(52) U.S. Cl.
CPC ......... *G16H 30/20* (2018.01); *G06T 17/00* (2013.01); *G16H 30/40* (2018.01); *G16H 50/20* (2018.01);
(Continued)

(58) Field of Classification Search
CPC ........ G16H 30/20; G16H 30/40; G06T 17/00
See application file for complete search history.

(56) References Cited

U.S. PATENT DOCUMENTS

| 9,697,601 B1 * | 7/2017 | Lliestrøle | G16H 30/20 |
| 2008/0229234 A1 * | 9/2008 | Astolfi | G06F 16/957 |
| | | | 707/E17.119 |
| 2015/0049081 A1 * | 2/2015 | Coffey | G06T 19/006 |
| | | | 345/419 |

FOREIGN PATENT DOCUMENTS

CN 104271066 A 1/2015

OTHER PUBLICATIONS

Lockhart, Shawna. Tutorial Guide to AutoCAD 2014. SDC Publications, 2013. 5 pages (Year: 2013).*

* cited by examiner

*Primary Examiner* — David F Dunphy
(74) *Attorney, Agent, or Firm* — Canon U.S.A., Inc. IP Division (57) ABSTRACT

The present disclosure provides a medical image processing apparatus capable of readily creating, from a medical image, an electronic document that displays a three-dimensional body organ model. The medical image processing apparatus performs control to acquire patient information from DICOM additional information of medical image data designated when the creation of the electronic document has been instructed, and to create the electronic document of the three-dimensional body organ model corresponding to the medical image data, the electronic document containing the
(Continued)

acquire patient information. To which patient the three-dimensional body organ model belongs can be identified on the electronic document.

15 Claims, 9 Drawing Sheets

Related U.S. Application Data continuation of application No. PCT/JP2016/081979, filed on Oct. 28, 2016.

(51) Int. Cl.
  *G16H 50/50* (2018.01)
  *G16H 50/20* (2018.01)
  *G16H 30/40* (2018.01)
  G09B 23/28 (2006.01)
  G16H 10/60 (2018.01)
  G06T 7/00 (2017.01)
  G09B 23/30 (2006.01)

(52) U.S. Cl.
  CPC .......... *G16H 50/50* (2018.01); *G06T 7/0012* (2013.01); *G06T 2207/30004* (2013.01); *G06T 2210/41* (2013.01); *G09B 23/286* (2013.01); *G09B 23/30* (2013.01); *G16H 10/60* (2018.01)

| | LAYER 1 | LAYER 2 | LAYER 3 | LAYER 4 | LAYER 5 | LAYER 6 |
|---|---|---|---|---|---|---|
| DISPLAY | ON | ON | ON | ON | OFF | OFF |
| NAME | HEART | MAIN ARTERY | LEFT CORONARY ARTERY | RIGHT CORONARY ARTERY | | |
| DISPLAY COLOR | RED | YELLOW | BLUE | VIOLET | | |

| NAME | ○○ TARO | ID | 123456 |
|---|---|---|---|
| INSPECTION DATA | 2015/10/30 | BIRTH DAY | 1946/8/4 |
| AGE | 69Y | GENDER | M |
| REMARKS | | | |

```
⊟ model  ~1001
  ☐ HEART
  ☑ MAIN ARTERY
  ☑ LEFT CORONARY ARTERY
  ☑ RIGHT CORONARY ARTERY
```

MEDICAL IMAGE PROCESSING APPARATUS, PROGRAM INSTALLABLE INTO MEDICAL IMAGE PROCESSING APPARATUS, AND MEDICAL IMAGE PROCESSING METHOD

CROSS-REFERENCE TO RELATED APPLICATIONS

This application is a continuation of U.S. application Ser. No. 15/965,159, filed Apr. 27, 2018, which is a continuation of International Patent Application No. PCT/JP2016/081979, filed Oct. 28, 2016, which claims priority to Japanese Patent Application No. 2015-213479, filed Oct. 29, 2015; to Japanese Patent Application No. 2015-213477, filed Oct. 29, 2015; and to Japanese Patent Application No. 2015-213478, filed Oct. 29, 2015, all of which are hereby incorporated by reference herein in their entireties.

BACKGROUND

Technical Field

The present disclosure relates to a medical image processing apparatus, a medical image processing method, and a program installable into the medical image processing apparatus.

Background Art

Recently, medical practices of creating a three-dimensional image of a human body from a medical image that has been captured by medical apparatuses, such as an MRI (Magnetic Resonance Imaging) apparatus and an X-ray CT (Computed Tomography) apparatus, and of utilizing the three-dimensional image in treatment and diagnosis have been widely conducted in the field of medical care. Patent Literature (PTL) 1 discloses a medical image diagnosis apparatus capable of specifying a tumor range on the basis of a three-dimensional image, which has been created from a medical image, even for a visually unrecognizable tumor, and of aiding to determine an excision range.

By using a high-performance computer, the three-dimensional image created from the medical image can be presented in a manner of allowing the image to be rotated optionally, or under desired display conditions through rendering processing. On the other hand, there is also a demand for a technique of enabling the three-dimensional image to be reviewed even in, for example, an operating room in which the high-performance computer is not equipped. A method of outputting a three-dimensional body organ model as an electronic document in the PDF format, for example, can be used as an example of the technique of displaying the three-dimensional image with a general-purpose computer.

CITATION LIST

Patent Literature

PTL 1 Japanese Patent Laid-Open No. 2009-61035

In a medical image processing apparatus of related art, however, creating the electronic document capable of displaying the above-described three-dimensional body organ model has been considerably intricate because a user is required to perform the task of causing the computer to create surface shape data from a medical image that has been captured by medical apparatuses, such as an MRI (Magnetic Resonance Imaging) apparatus and an X-ray CT (Computed Tomography) apparatus, to output the surface shape data in the file format readable as an electronic document, and to read the surface shape data as the electronic document.

SUMMARY

In view of the above-mentioned state of the art, an object of the present disclosure is to provide a technique capable of readily creating an electronic document that is able to display a three-dimensional body organ model from a medical image. In particular, an object of the present disclosure is to provide a technique capable of creating an electronic document in such a manner that a user can identify to which patient information represented by the three-dimensional body organ model belongs.

To achieve the above objects, the present disclosure provides a medical image processing apparatus of creating an electronic document used to display a three-dimensional body organ model, the medical image processing apparatus including an accepting unit that accepts an instruction of designating medical image data and creating an electronic document corresponding to the medical image data, an acquisition unit that acquires patient information from DICOM additional information of the medical image data designated when the creation of the electronic document has been instructed through the accepting unit, and a control unit that performs, in response to the electronic-document creation instruction accepted by the accepting unit, control to create the electronic document of the three-dimensional body organ model corresponding to the medical image data, the relevant electronic document containing the patient information acquired by the acquisition unit.

Further features of the present disclosure will become apparent from the following description of exemplary embodiments with reference to the attached drawings.

DESCRIPTION OF EMBODIMENTS

A method of outputting an electronic document capable of displaying a three-dimensional body organ model by using medical three-dimensional image data, which is created from volume data (plurality of slice image data) captured by a medical image diagnosis apparatus (modality apparatus), will be described in detail below with reference to the drawings.

The modality apparatus usable in this embodiment and capable of capturing a medical image is, for example, an MRI (Magnetic Resonance Imaging) apparatus, an X-ray CT (Computed Tomography) apparatus, a PET (Positron Emission Tomography) apparatus, or an ultrasonic diagnosis apparatus. Medical image data captured by that modality apparatus is stored in conformity with standards, called the DICOM (Digital Imaging and Communication in Medicine) standards, designed to standardize communication protocols and data formats for medical images. The data in conformity with the DICOM standards is made up of a region where image data such as slice image data is stored, and a region where additional information related to the image data is stored. The DICOM additional information contains not only patient information regarding a patient who is an object in capturing the image data, such as patient name, patient ID, inspection date, birth day, age, and body shape information, but also information regarding conditions in capturing the image data. That medical image data is stored in an image server, which is generally called a PACS (Picture Archiving and Communication System) in a hospital, to be utilizable in various departments of the hospital. In these days, the PACS has also been built into a cloud service.

This embodiment is described in connection with an example in which a data format of an electronic document created by using the medical image data is the PDF format, but the data format is not limited to the PDF format insofar as being able to display a three-dimensional body organ model.

Figure 1A:
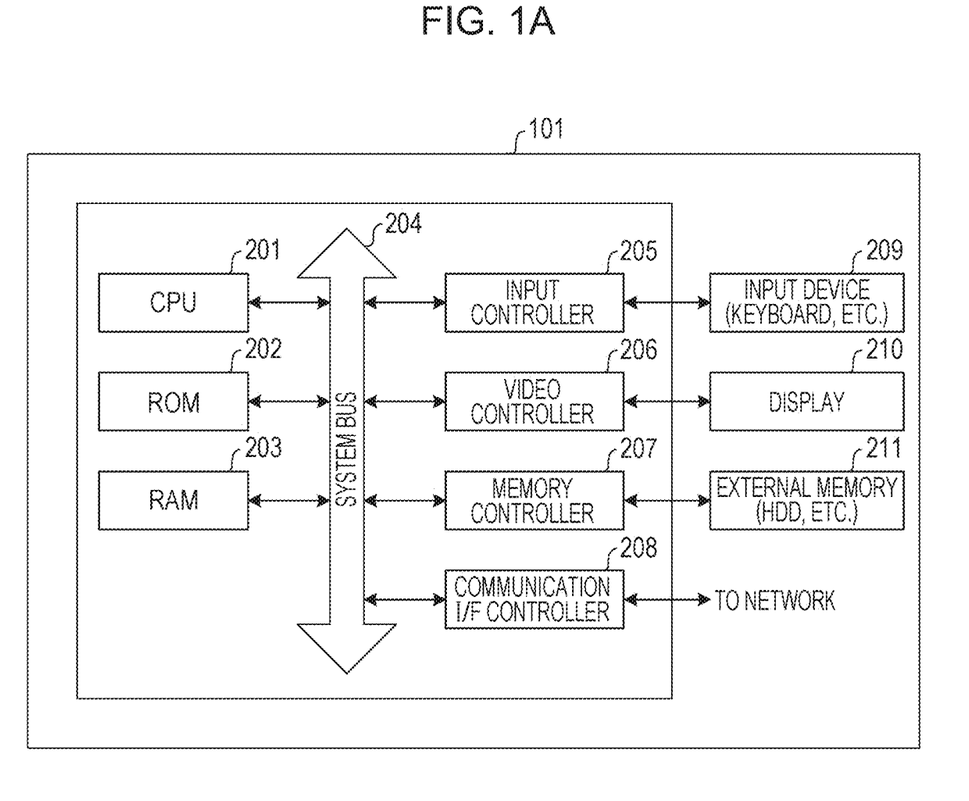
FIGS. 1A and 1B are block diagrams representing examples of a hardware configuration and a functional configuration of a medical image processing apparatus 101.

FIG. 1A is a block diagram representing an example of a hardware configuration of a medical image processing apparatus 101 (also called an "information processing apparatus") according to this embodiment. The medical image processing apparatus 101 according to this embodiment is configured to acquire (read) volume data created on the basis of image data that has been captured by the medical image processing apparatus, and to execute image processing of a medical three-dimensional image. Processing to create medical three-dimensional image data may be executed by the medical image processing apparatus 101 or by another processor in advance.

A CPU 201 performs centralized control over individual devices and controllers connected to a system bus 204.

A ROM 202 or an external memory 211 (storage unit) stores not only control programs for the CPU 201, such as BIOS (Basic Input/Output System) and an operating system program (called "OS" hereinafter), but also other various programs, described later, necessary for realizing the functions executed by the medical image processing apparatus 101. A RAM 203 functions as a main memory, a work area, etc. for the CPU 201.

The CPU 201 performs various operations by loading the programs, which are needed to execute the processing, into the RAM 203, and by executing the loaded programs.

An input controller (Input C) 205 controls inputs from an input device 209, for example, a keyboard or a pointing device such as a mouse (not illustrated).

A video controller (VC) 206 controls display of images onto a display unit such as a display 210. The display unit may be a CRT or a liquid crystal display, but the type of the display unit is not limited to those examples.

A memory controller (MC) 207 controls accesses to a hard disk (HD), a flexible disk (FD), or an external memory 211, such as a card memory, connected to a PCMCIA card slot through an adaptor, those disks and those memories storing a boot program, browser software, various applications, font data, user files, editing files, various data, etc.

A communication I/F controller (Communication I/F C) 208 establishes connection to and performs communication with an external unit, such as a storage device, which stores images acquired by a medical image diagnosis apparatus, such as a CT apparatus, via a network, and further executes communication control processing in the network. For example, Internet communication using TCP/IP can be performed.

The CPU 201 enables images to be displayed on the display 210 by executing a rendering (rasterization) process of outline font into a display information region within the RAM 203, for example.

Moreover, the CPU 201 enables a user to enter an instruction by using, for example, a mouse cursor (not illustrated) on the display 210.

Various programs, etc. used to execute various types of processing (described later) by the medical image processing apparatus 101 according to some embodiments are recorded in the external memory 211 and are executed by the CPU 201 by being loaded into the RAM 203 as the occasion requires.

Definition files and various information tables used when executing the programs in some embodiments are also stored in the external memory 211.

Figure 1B:
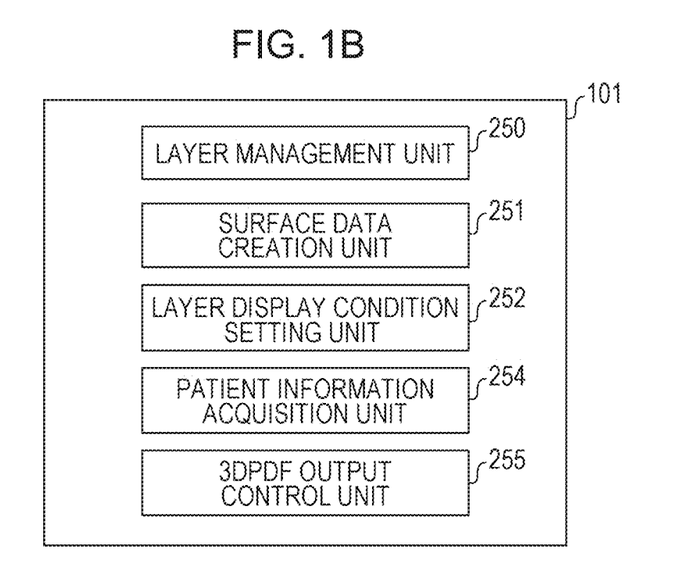

FIG. 1B is a block diagram representing a functional configuration of the medical image processing apparatus 101. The CPU in the medical image processing apparatus 101 functions as a layer management unit 250, a surface data creation unit 251, a layer display condition setting unit 252, a patient information acquisition unit 253, and a 3DPDF output control unit 254.

The layer management unit 250 manages regions specified from the medical image data, which has been captured by the medical image diagnosis apparatus, as a layer for each of the regions. Here, the layer management unit 250 may be a functional unit that manages, as a layer, each region extracted on the basis of automatic extraction conditions having been set and managed in advance corresponding to analysis software, or that manages, as a layer of a three-dimensional body organ model, each region specified by the user from the medical image data.

The surface data creation unit 251 (surface shape creation unit) is a functional unit capable of converting the medical three-dimensional image data to surface shape data. When a body organ for which an electronic document is to be output is divided into a plurality of layers, the surface data creation unit 251 can perform the conversion to the surface shape data divided per region corresponding to each layer. Suitable one of the known techniques, for example, the Marching cubes algorithm, can be used as a method of converting the medical image data to the surface shape data.

The layer display condition setting unit 252 is a functional unit for setting display conditions as to how the three-dimensional body organ model is to be displayed on the electronic document. The layer display condition setting unit 252 can set display conditions, such as a layer display color for each of layers constituting the three-dimensional body organ model and a layer name (display name). Those display conditions may be set by acquiring the layer display color and the layer name that have been set in advance corresponding to the analysis software, or may be set by acquiring the layer display color and the layer name that are set by the user.

The patient information acquisition unit 253 is a functional unit that acquires the patient information, such as the patient name, the patient ID, the inspection date, the birth day, the age, and the gender, from the DICOM additional information of the medical three-dimensional image data to be output as the electronic document.

The 3DPDF output control unit 254 (electronic document creation control unit) is a functional unit that executes control to output the electronic document in the PDF format, which can display the three-dimensional body organ model, on the basis of the surface shape data created by the surface data creation unit 251. The three-dimensional body organ models divided into a plurality of layers can be output together as the electronic document. It is also possible to control outputting of the electronic document in a manner of displaying the display conditions acquired by the layer display condition setting unit and the patient information acquired by the patient information acquisition unit as well.

Figure 5:
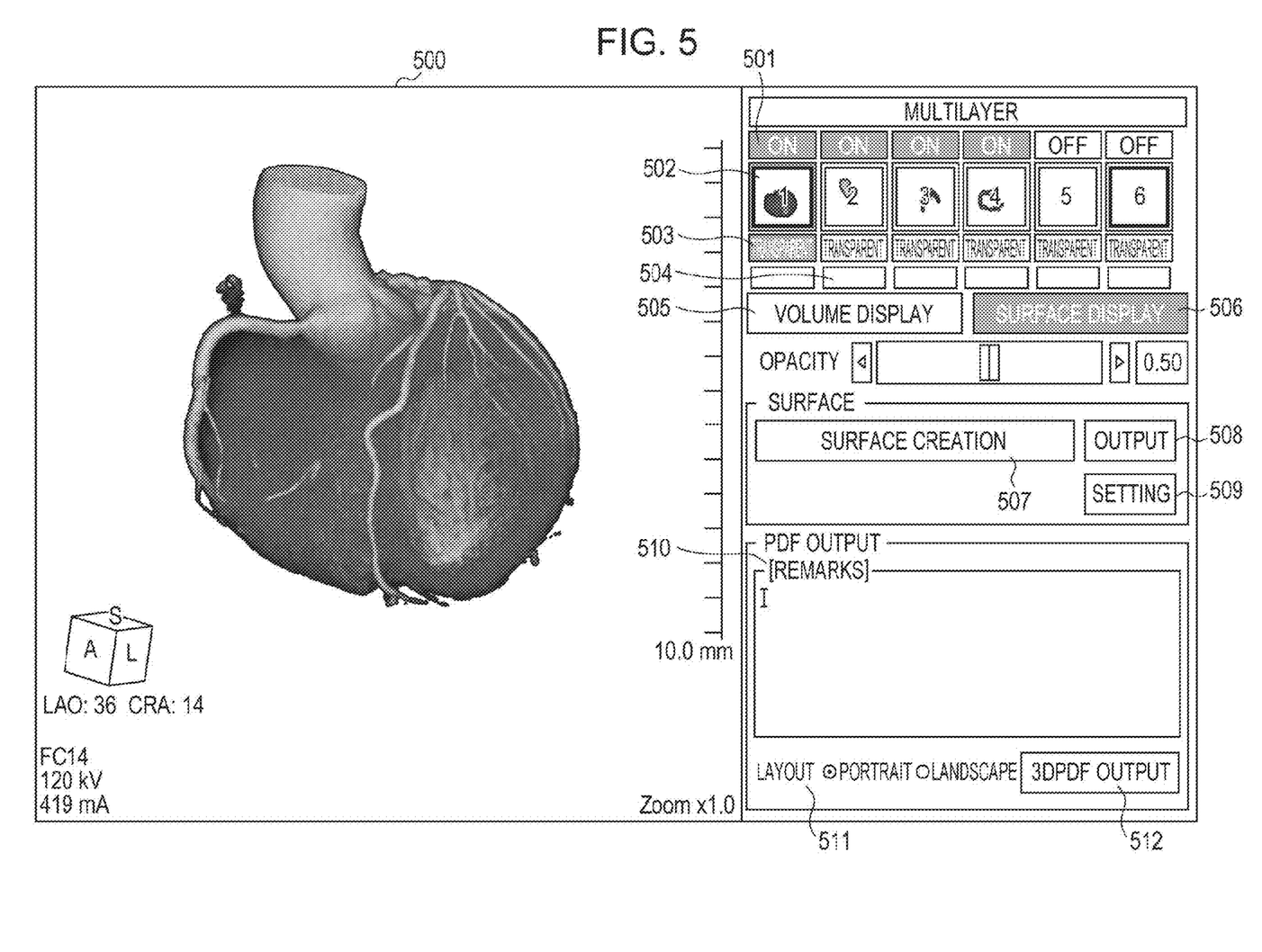
FIG. 5 illustrates an example of a screen displayed by the medical image processing apparatus when it outputs an electronic document.

FIG. 5 illustrates an example of a screen displayed by the medical image processing apparatus according to some embodiments, on which the user can instructs creation of the electronic document. This embodiment is described in connection with an example in which the medical three-dimensional image data for a region including a heart is output as the electronic document.

In the case of targeting, for example, the region including the heart (called the "heart region" hereinafter), the medical image processing apparatus 101 is configured to be able to manage the heart region while dividing it into a plurality of layers called "right coronary artery", "left coronary artery", "heart", and "main artery", and to make switching between a display mode and a non-display mode upon selection of a display button 501 on the display per layer. In the case of outputting the 3DPDF, the medical image processing apparatus 101 can make control to output, as the three-dimensional body organ model, the layer for which the display mode is selected by the display button 501, and not to output, as the three-dimensional body organ model, the layer for which the non-display mode is selected. The layer may be set as a region that is extracted by the user from the medical three-dimensional image data. Alternatively, when the analysis software started up in displaying the medical three-dimensional image data performs management in a manner of extracting a predetermined region in advance (namely, when the medical image processing apparatus 101 includes an extraction condition management unit), the layer may be set as the region extracted in accordance with those extraction conditions.

Figure 6A:
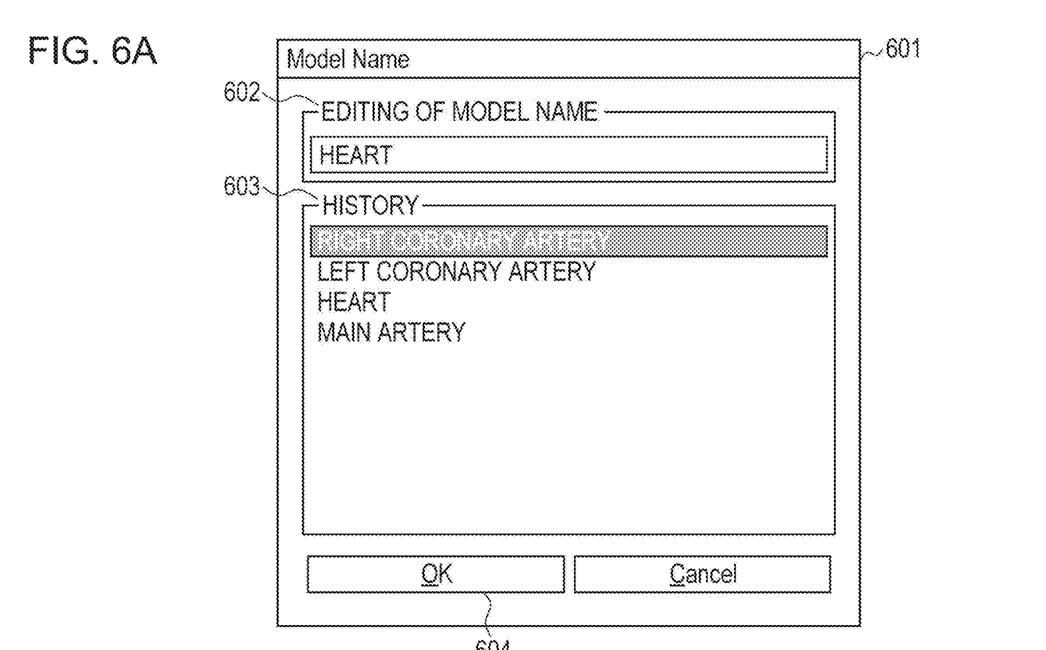
FIG. 6A illustrates an example of a screen for setting a name of a body organ model.

A thumbnail image display portion 502 is a display portion capable of displaying a thumbnail image of the region set as the layer, and it can be further used to set the layer name. More specifically, when the thumbnail image display portion 502 is selected, a layer name setting screen 601 illustrated in FIG. 6A is displayed. The layer name can be set by entering a desired layer name in an entry field 602, and by pressing an OK button 604. Furthermore, because the names entered in the past are displayed in a history field 603, the layer name can also be set by selecting one of the names displayed in the history field 603. The layer name can be set per layer. Instead of setting the layer name on the layer name setting screen 601 by the user, the layer name may be set as a preset name when a name corresponding to each region is set in advance by the analysis software started up in displaying the medical three-dimensional image data.

Figure 6B:
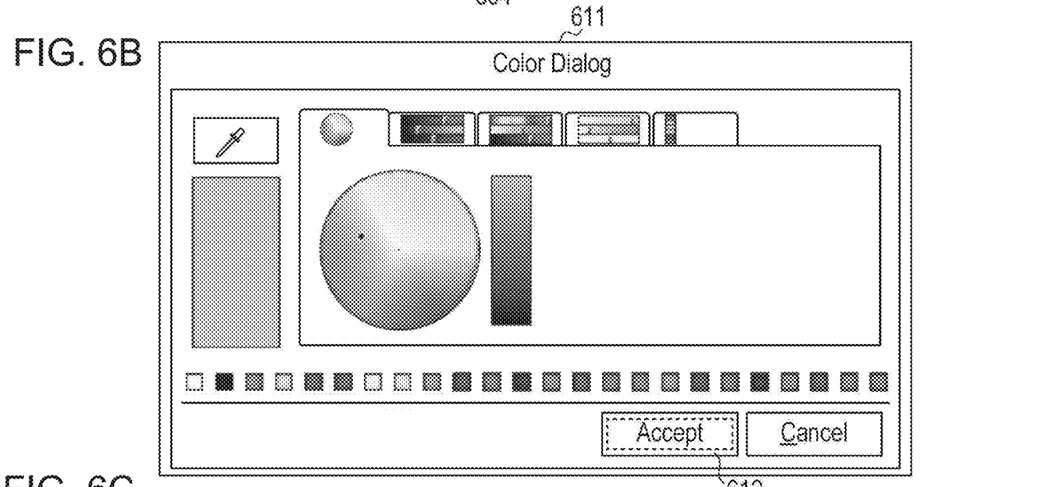
FIG. 6B illustrates an example of a screen for setting a display color of the body organ model.

A layer display color setting portion 504 is a setting portion capable of setting a layer display color when surface display is performed. When the layer display color setting portion 504 is selected, a color adjustment pallet 611 illustrated in FIG. 6B is displayed, and the layer display color can be set by selecting a desired color in the color adjustment pallet 611, and by pressing an Accept button 612. The layer display color can be set per layer. Instead of setting the layer display color as a display color selected by the user, the layer display color may be set as a preset display color when a display color corresponding to each region is set in advance by the analysis software started up in displaying the medical three-dimensional image data.

Figure 6C:
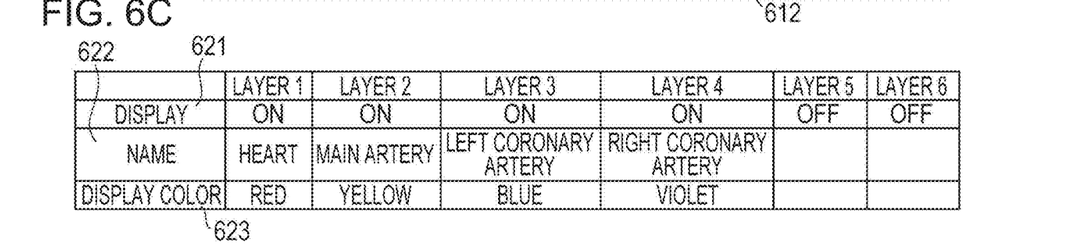
FIG. 6C illustrates an example of a table for managing layer information having been set.

FIG. 6C illustrates an example of a table for managing, per layer, layer information including the layer name and the layer display color, which have been set as described above. As illustrated in FIG. 6C, the table stores, per layer, an item 621 for switching between the display mode and the non-display mode, an item 622 indicating the set name, and an item 623 indicating the set display color.

Figure 7:
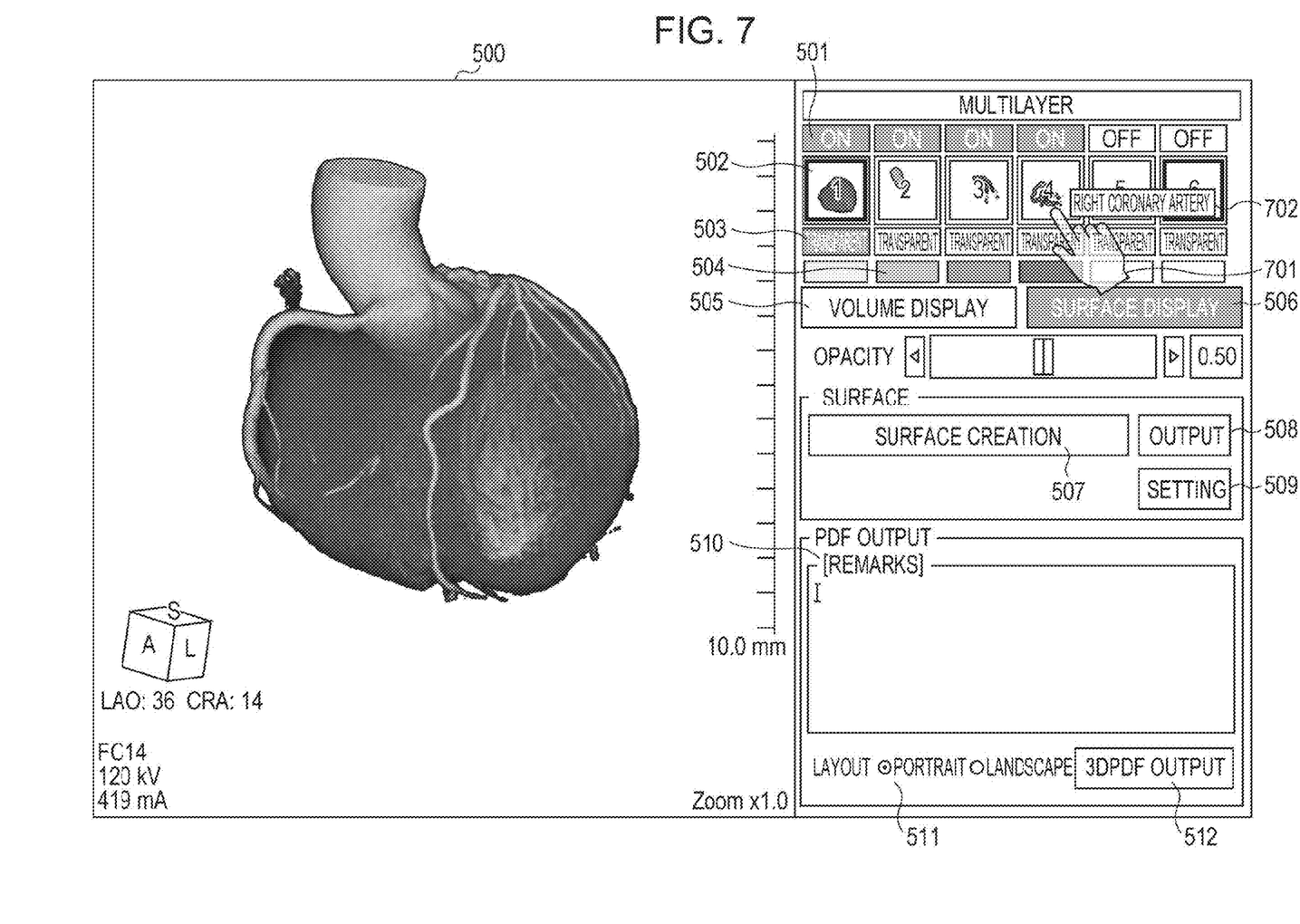
FIG. 7 illustrates an example of a screen displayed by the medical image processing apparatus when it outputs an electronic document.

FIG. 7 illustrates an example of a screen displayed by the medical image processing apparatus, the screen representing a state after the layer name and the layer display color have been set. When a mouse pointer 701, for example, is placed over an area of the thumbnail image display portion 502 where the layer name is set, a set layer name 702 is displayed.

A transparent-state setting button 503 is a button with which the user can switch over whether a volume rendering image to be displayed in a display region 500 is presented in a transparent state or an opaque state per layer.

A volume display button 505 and a surface display button 506 are buttons with which the user can switch over whether an image obtained through volume rendering of the medical three-dimensional image data or an image obtained by converting the medical three-dimensional image data to the surface shape data is to be displayed in the display region 500 for the medical three-dimensional image data. The surface display button 506 is designed such that it cannot be selected when the surface shape data is not yet created.

A surface creation button 507 is a button with which the user can instruct a process of converting the medical three-dimensional image data to the surface shape data. When that conversion process is executed and the surface shape data is created, the created surface shape data is stored in the storage unit such as the external memory 211. By storing the surface shape data into the storage unit, a surface creation process can be avoided from being repeatedly executed on the same medical three-dimensional image data.

Figure 8:
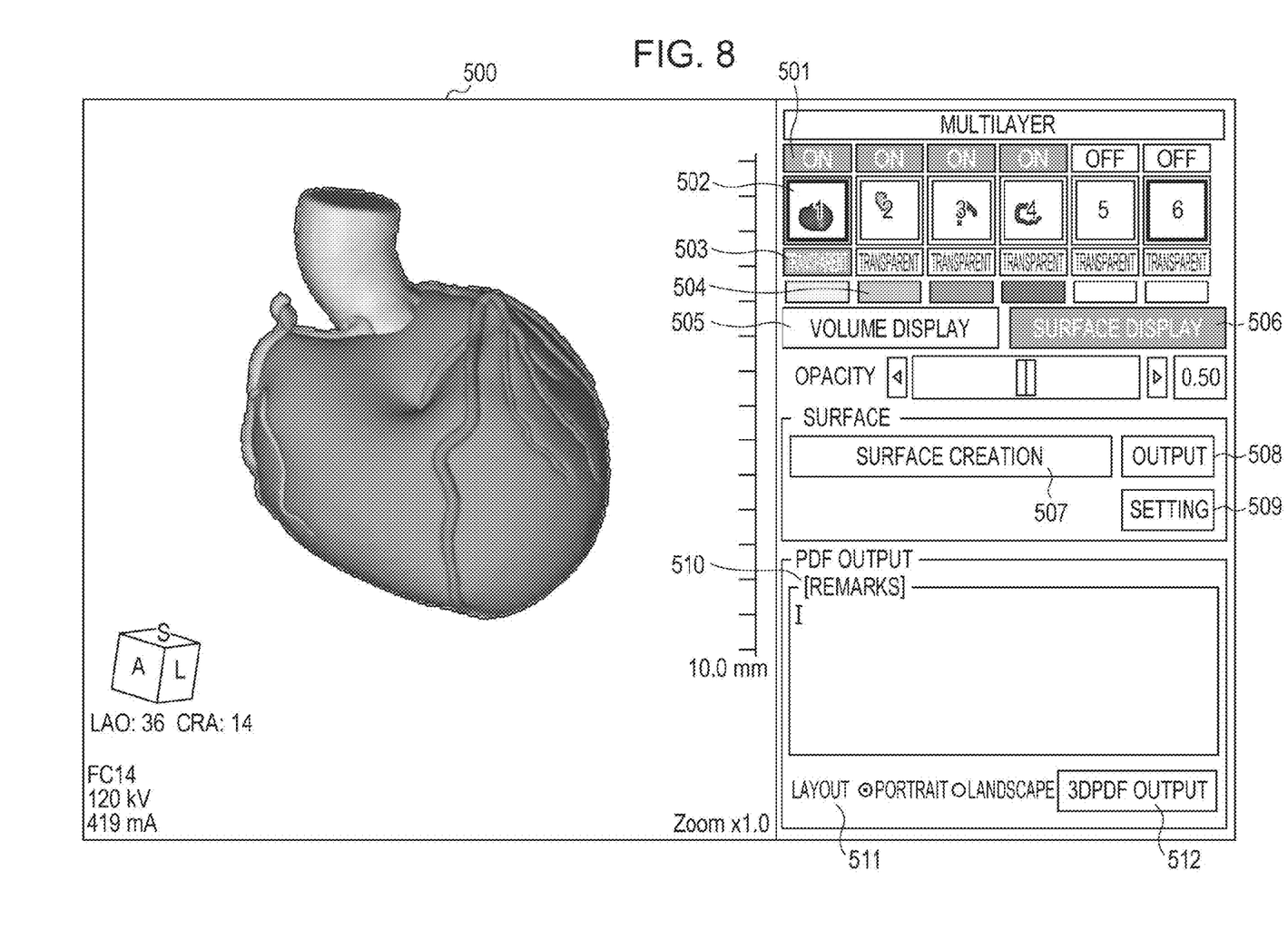
FIG. 8 illustrates an example of a screen displayed by the medical image processing apparatus when it outputs an electronic document.

FIG. 8 illustrates an example of a screen displayed by the medical image processing apparatus when the surface display button 506 is selected after the surface creation process has been executed. In the illustrated example, the three-dimensional body organ model of the surface shape data, which has been created from the medical three-dimensional image data, is displayed in the display region 500. Display colors in individual regions of the three-dimensional body organ model displayed at that time are the display colors set by the layer display color setting portion 504.

An output button 508 is a button with which the user can output, as a file, the surface shape data created through the surface creation process. The surface shape data can be output as data in the STL format, the IDTF format, or the VRML format, for example. The output data can be used in manually creating an electronic document by the user, or in performing a modeling process by a three-dimensional printer. A setting button 509 is a button with which the user can set the conditions and the storage destination when the surface creation process is executed.

A remarks entry field 510 is an entry field (entry unit) where the user can enter comments, etc. to be added at the time of outputting the electronic document. A layout select button 511 enables the user to select whether the electronic document is output in a portrait- or landscape-oriented form. A 3DPDF output button 512 is a button with which the user can instruct outputting of the electronic document including the three-dimensional body organ model, which corresponds to the image displayed in the PDF format in the display region 500. When the 3DPDF output button 512 is pressed, the electronic document corresponding to the medical three-dimensional image data displayed in the display region 500 at that time is output. The electronic document is output such that the name and the display color of each layer of the three-dimensional body organ model to be represented on the electronic document are given as the name set by the thumbnail image display portion 502 and the color set by the layer display color setting portion 504, respectively.

Figure 2:
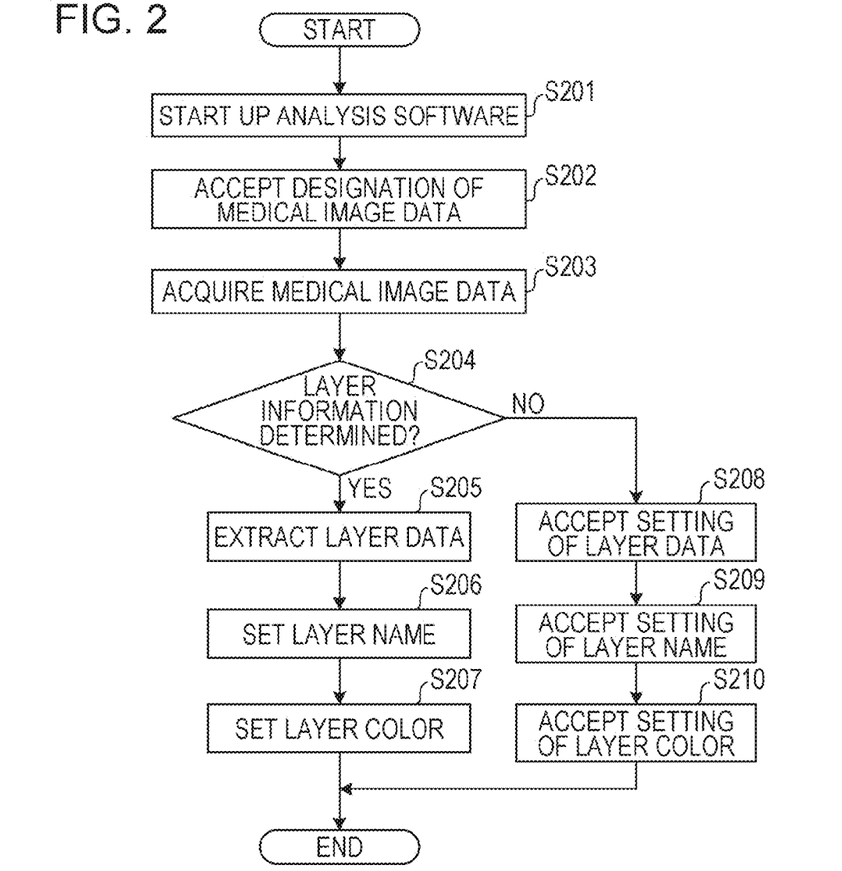
FIG. 2 is a flowchart referenced to explain a flow of medical image processing according to an embodiment.

A flow of processing until the layer name and the layer display color of each region specified from the medical image data are set will be described below with reference to a flowchart of FIG. 2. The processing illustrated in the flowchart of FIG. 2 is executed by the CPU 201 in the medical image processing apparatus 101 reading and executing the stored control program.

In S201, the CPU 201 in the medical image processing apparatus 101 starts up the analysis software designated by the user. More specifically, the CPU 210 may start up analysis software in which body-organ extraction conditions and layer display conditions are set, such as "heart analysis software" and "liver analysis software", or analysis software in which no conditions are set, such as free analysis software.

In S202, the CPU 201 in the medical image processing apparatus 101 accepts, from the user, designation of the medical image data to be displayed. Because the medical image data is generally stored in the PACS (image server) as described above, the medical image processing apparatus 101 is able to designate not only data stored in the medical image processing apparatus, but also data stored in the external PACS (image server), etc. While the above description is made in connection with an example of designating the medical image data after starting up the analysis software, not all embodiments are limited to such an example, and the analysis software may be started up after designating the medical image data.

In S203, the CPU 201 in the medical image processing apparatus 101 acquires the medical image data designated in S202 from the storage unit in which the medical image data is stored.

In S204, the CPU 201 determines whether layer conditions, such as the extraction conditions and the display conditions for the body organs, are set in the analysis software started up in S201. If the layer conditions are set, the processing is advanced to S205 through S207. More specifically, a region is extracted in accordance with the set extraction conditions and is set as a layer (S205). A layer name is set in accordance with the set display conditions (S206), and a layer display color is set in accordance with the set display conditions.

On the other hand, if the layer conditions are not set, the processing is advanced to S208 through S210. More specifically, the CPU 201 accepts the setting of a region defined as a layer from the user (S208), accepts the setting of a layer name from the user (S209), and accepts the setting of a layer display color from the user (S210).

Alternately, it is also possible to automatically extract the layer, and to manually set the layer name and/or the layer display color by the user. The task of setting the layer name and/or the layer display color is not essential. When the layer name and/or the layer display color is not set, the relevant information is merely not reflected on the electronic document.

Figure 3:
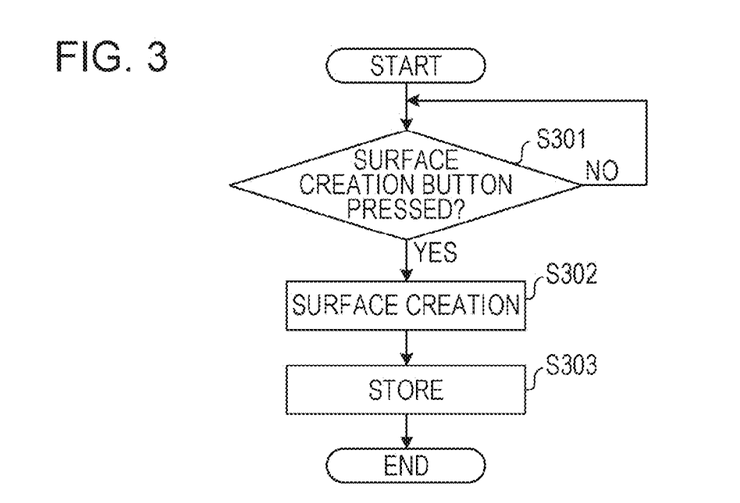
FIG. 3 is a flowchart referenced to explain a flow of medical image processing according to an embodiment.

A flow of a surface shape creation process executed upon pressing of the surface creation button 507 will be described below with reference to a flowchart of FIG. 3. Processing illustrated in the flowchart of FIG. 3 is executed by the CPU 201 in the medical image processing apparatus 101 reading and executing the stored control program.

In S301, the CPU 201 in the medical image processing apparatus 101 determines whether the surface creation button 507 is pressed. If it is determined that the surface creation button 507 is pressed, the processing is advanced to S302 in which the CPU 201 in the medical image processing apparatus 101 creates the surface shape data per layer set in S205 or per layer set in S208. In practice, each layer can be converted to the surface shape data by using suitable one of the known techniques, for example, the Marching cubes algorithm.

In S303, the CPU 201 in the medical image processing apparatus 101 stores the surface shape data, which has been created in S302, at a preset location in the storage unit. In practice, apex coordinates obtained with the Marching cubes algorithm, for example, are stored as the surface shape data.

After the end of the above-described processing, the CPU 201 can display the three-dimensional body organ model, which has been created on the basis of the surface shape data, in the display region 500 when the surface display button 506 is pressed, or to output a file when the output button 508 is pressed.

Figure 4:
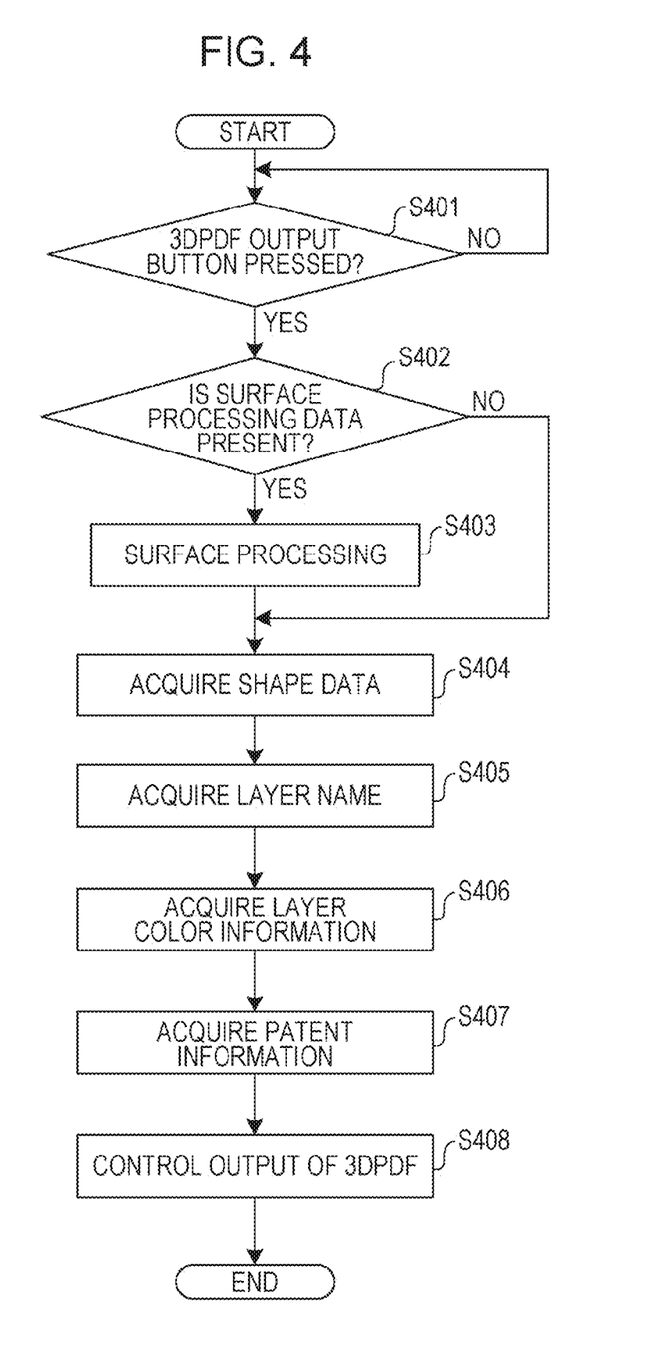
FIG. 4 is a flowchart referenced to explain a flow of medical image processing according to an embodiment.

A flow of processing executed upon pressing of the 3DPDF output button 512 will be described below with reference to a flowchart of FIG. 4. The processing illustrated in the flowchart of FIG. 4 is executed by the CPU 201 in the medical image processing apparatus 101 reading and executing the stored control program.

In S401, the CPU 201 in the medical image processing apparatus 101 determines whether the 3DPDF output button 512 is pressed. If it is determined that the 3DPDF output button 512 is pressed, the processing is advanced to S402 in which the CPU 201 in the medical image processing apparatus 101 determines whether the surface creation button 507 has been pressed and the surface shape data (surface processing data) has been created in the past. In practice, the above point can be determined by checking whether the surface shape data is stored at the preset location in the storage unit.

If it is determined in S402 that the surface shape data has been created in the past, the processing is advanced to S404 without executing the creation process again. If it is determined in S402 that the surface shape data has not been created in the past, the CPU 201 in the medical image processing apparatus 101 creates, as in S302, the surface shape data per layer set in S205 or per layer set in S208, and stores the surface shape data at the preset location in the storage unit. Thus, when surface shape processing has been executed in the past, the surface shape processing can be omitted in the process of creating the 3DPDF, and a time taken to create the electronic document can be cut down.

In S404, the CPU 201 in the medical image processing apparatus 101 acquires, from the storage unit, the surface shape data of the layer that is set to the display mode by the display button 501, the surface shape data having been created in S403 or S302. In S405, the CPU 201 in the medical image processing apparatus 101 acquires the name of the layer that is set to the display mode by the display button 501, the layer name having been set in S206 or S209. In S406, the CPU 201 in the medical image processing apparatus 101 acquires the display color of the layer that is set to the display mode by the display button 501, the layer display color having been set in S207 or S210. The above-described setting data can be acquired from the table illustrated in FIG. 6C, for example.

In S407, the CPU 201 in the medical image processing apparatus 101 acquires the patient information, such as the patient name, the patient ID, the inspection date, the birth day, the age, and the gender, from the DICOM additional information of the medical image data designated in S202.

In S408, the CPU 201 in the medical image processing apparatus 101 performs control to output the electronic document in the PDF format capable of displaying the three-dimensional body organ model by using the surface shape data acquired in S404, the layer name acquired in S405, the layer display color acquired in S406, and the patient information acquired in S407.

While the surface shape data, the layer name, and the layer display color are separately acquired in the above-described example, those data may be collected, before outputting them, together into one file to be usable when the electronic document is created from the relevant file and the DICOM additional information. For example, the IDTF format or the VRML format can be used as a format of the file that is output in the collected form.

Through the above-described operations, the user can create the electronic document corresponding to the desired medical image data. As a result, the user can check the three-dimensional state of the body organ for aid in carrying out treatment and diagnosis even in, for example, an operating room where a high-performance computer is not installed.

Figure 9:
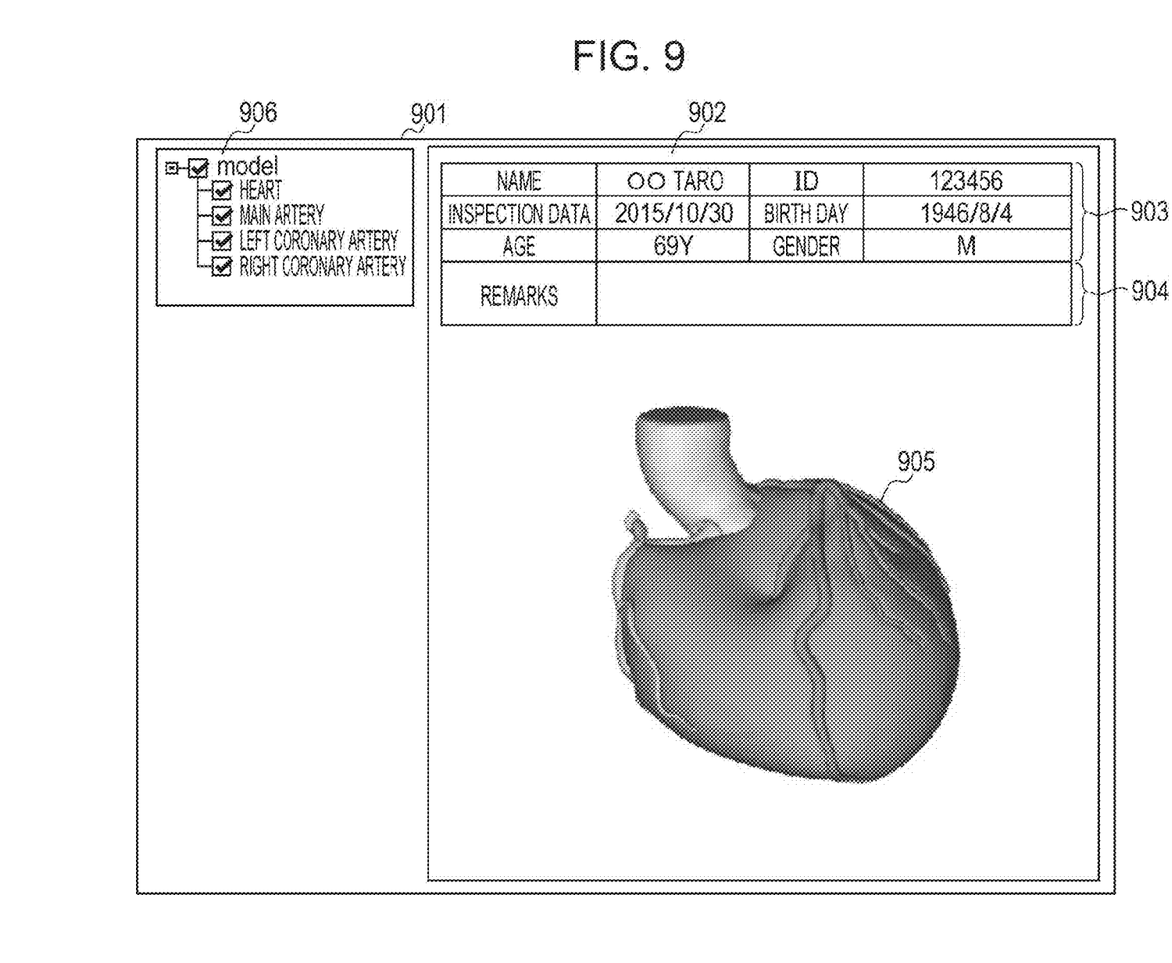
FIG. 9 illustrates an example of a screen displayed by the medical image processing apparatus when it outputs an electronic document.
Figure 10:
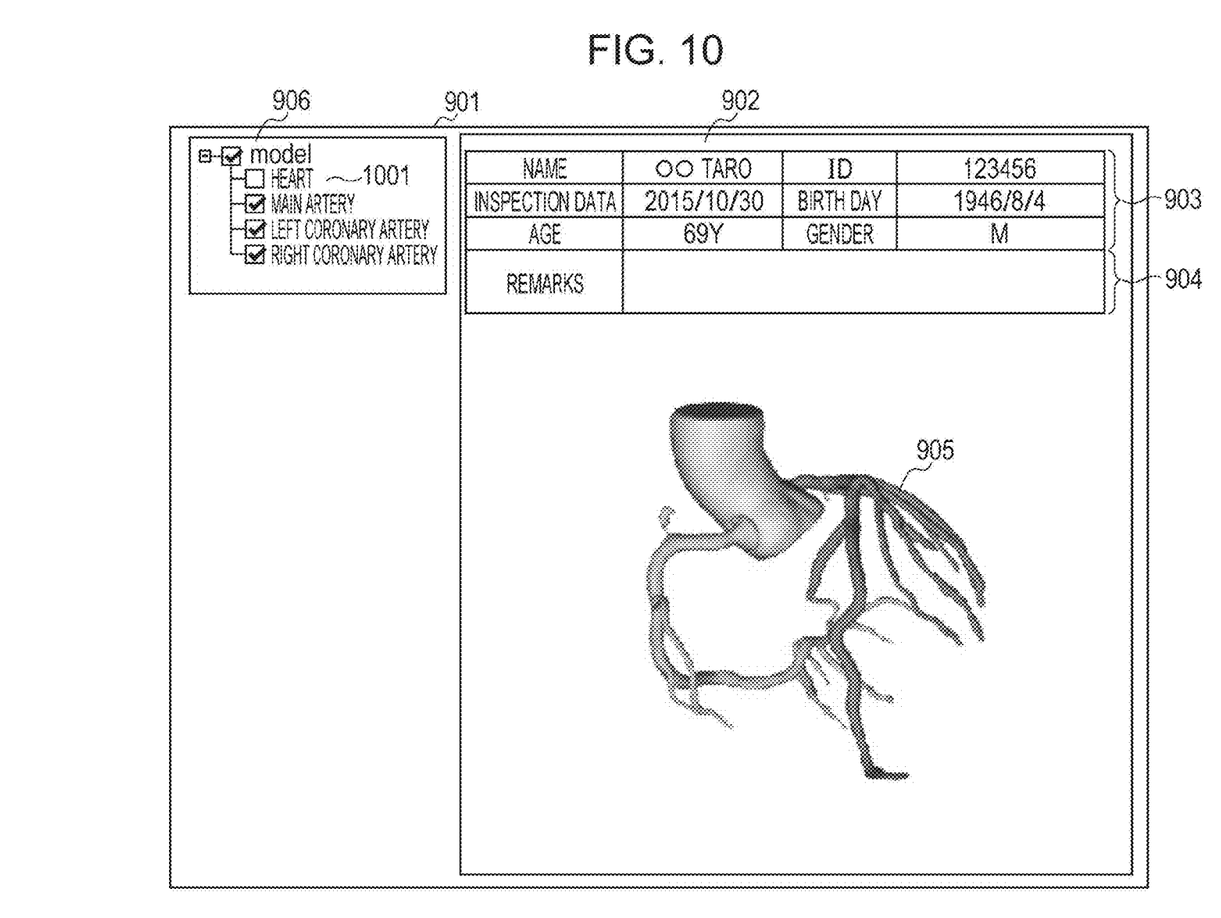
FIG. 10 illustrates an example of a screen displayed by the medical image processing apparatus when it outputs an electronic document.

FIGS. 9 and 10 each illustrate an example of a state in which an electronic document 902 output through the processing illustrated in FIG. 4 is displayed on an electronic document viewer 901.

The electronic document viewer 901 includes a region where the electronic document 902 is displayed, and a select region 906 where the user selects a display model of the electronic document to be displayed. The electronic document 902 includes a three-dimensional body organ model 905, a patient information field 903, and a remarks field 904.

The select region 906 includes a check box for enabling the display or non-display mode to be selected (switched over) per layer. Furthermore, the name corresponding to the layer is displayed in the select region 906. A body organ region corresponding to the checked layer is displayed as the three-dimensional body organ model 905 on the electronic document 902, while a body organ region corresponding to the unchecked layer is not displayed as the three-dimensional body organ model 905 on the electronic document 902. FIG. 10 illustrates a state of the electronic document 902 when the layer of "HEART" in the select region 906 is unchecked. In the three-dimensional body organ model 905 on the electronic document 902 illustrated in FIG. 10, the heart region is not displayed. Moreover, the three-dimensional body organ model 905 is created such that regions of the body organs corresponding to the layers are each displayed in the set display color. Thus, since the display mode and the non-display mode can be switched over per layer, the user enables only the desired body organ model to be displayed or not displayed on the electronic document by designating the relevant body organ.

The patient information acquired in S407 is displayed in the patient information field 903. To which patient the electronic document belongs can be easily identified by displaying the patient information corresponding to the three-dimensional body organ model 905 as described above. In addition, when the 3DPDF output button 512 is pressed, the comments having been entered in the remarks entry field 510 illustrated in FIG. 5 are reflected in the remarks field 904.

Some embodiments can be implemented in the form of, for example, a system, an apparatus, a method, a program, or a storage medium. More specifically, some embodiments may be a system made up of a plurality of devices, or an apparatus constituted by one device.

Some embodiments supply software programs for carrying out the functions of the above-described embodiments to a system or an apparatus directly or remotely. In some embodiments an information processing apparatus in the system or the apparatus carries out those functions by reading and executing program codes supplied thereto.

Accordingly, the program codes installed in the information processing apparatus to carry out the functions and the processing by the information processing apparatus also take part in implementing some embodiments. For that reason, some embodiments include computer programs to carry out the functions and the processing.

In the above case, the computer programs may be in the form of object code, programs executed by an interpreter, or script data supplied to OS, for example, insofar as having the functions of programs.

Examples of a recording medium used to supply the programs include a flexible disk, a hard disk, an optical disk, a magneto-optical disk, an MO, a CD-ROM, a CD-R, and a CD-RW. Other examples include a magnetic tape, a non-volatile memory card, a ROM, and a DVD (DVD-ROM or DVD-R).

As another method, the programs may be supplied as follows. A client computer makes an access to a home page on the Internet by using a browser installed therein. Then, the client computer downloads, from the home page, the computer programs themselves in some embodiments, or a file that contains the computer programs in compressed form and has an automatic installation function, onto a recording medium such as a hard disk.

Alternatively, the computer programs according to some embodiments may be supplied by dividing program codes constituting the programs into a plurality of files, and by downloading those files from different home pages. In other words, some embodiments further include a WWW server for downloading, to a plurality of users, the program files to carry out the functions and the processing with an information processing apparatus.

Moreover, the computer programs according to some embodiments may be supplied as follows. After encrypting the computer programs, the encrypted programs are stored in storage media, such as CD-ROM's, and are distributed to users. The user who has cleared the predetermined conditions is allowed to download key information, which is needed to decrypt the encrypted programs, from a home page via the Internet. Then, the encrypted programs are decrypted by using the downloaded key information, and the obtained programs are installed into an information processing apparatus.

The functions in the above-described embodiment are carried out by an information processing apparatus reading programs and executing the programs. Alternatively, an OS running on the information processing apparatus may execute part or the whole of actual processing in accordance with instructions of the read programs, and the functions in the above-described embodiment may be realized with the processing executed by the OS.

Furthermore, programs read from a recording medium may be written into a memory equipped in an add-on board inserted into an information processing apparatus, or in an add-on unit connected to an information processing apparatus. Then, a CPU or the like equipped on the add-on board or the add-on unit may execute part or the whole of actual processing in accordance with instructions of the written programs, and the functions in the above-described embodiment may be realized with the processing executed by the CPU or the like.

To which patient the information represented by the three-dimensional body organ model belongs can be identified by creating the electronic document that contains the patient information obtained from the DICOM additional information.

While the present disclosure has described to exemplary embodiments, it is to be understood that the claims are not limited to the disclosed exemplary embodiments. The scope of the following claims is to be accorded the broadest interpretation so as to encompass all such modifications and equivalent structures and functions.

The invention claimed is:

1. A medical image processing apparatus of generating an electronic document used to display a three-dimensional body organ model, the medical image processing apparatus comprising:
a memory storing instructions; and
at least one processor that, upon execution of the instructions, is configured to operate as:
an accepting unit that accepts an instruction for generating an electronic document;
a surface shape generation unit that generates surface shape data from medical image data and stores the surface shape data in a storage; and
a control unit that generates the electronic document with the three-dimensional body organ model using the surface shape data generated by the surface shape generation unit, in response to the instruction accepted by the accepting unit,
wherein the control unit determines, upon accepting the instruction, whether or not the surface shape data for the three-dimensional body organ model is stored in the storage,
wherein in the case where it is determined that the surface shape data is stored in the storage, the surface shape generation unit does not generate the surface shape data again, the control unit generates the electronic document with the three-dimensional body organ model using the surface shape data stored in the storage,
wherein in the case where it is determined that the surface shape data is not stored in the storage, the control unit generates the electronic document with the three-dimensional body organ model using the surface shape data after the surface shape generation unit generates the surface shape data, and
wherein the surface shape generation unit converts the medical image data to the surface shape data in accordance with Marching cubes algorithm.

2. The medical image processing apparatus according to claim 1, wherein the three-dimensional body organ model is managed in a state divided into a plurality of layers, and
the control unit performs control to generate, as one electronic document, the three-dimensional body organ model divided for each of the layers.

3. The medical image processing apparatus according to claim 2, wherein the accepting unit is able to accept an instruction of indicating which one of the layers is to be used to generate the electronic document.

4. The medical image processing apparatus according to claim 2, wherein the surface shape generation unit generates the surface shape data for each of the layers by converting the medical image data.

5. The medical image processing apparatus according to claim 2, wherein the at least one processor is further configured to operate as a color setting unit that sets a display color for each of the layers,
wherein the control unit performs control to generate the electronic document containing the surface shape data for each of the layers in the display colors set by the color setting unit.

6. The medical image processing apparatus according to claim 5, wherein the color setting unit displays, on a display, a screen for setting of the display color.

7. The medical image processing apparatus according to claim 2, wherein the at least one processor is further configured to operate as a name setting unit that sets a name of each of the layers,
wherein the control unit performs control to generate the electronic document containing the surface shape data for each of the layers having the names set by the name setting unit.

8. The medical image processing apparatus according to claim 7, wherein the accepting unit causes a list of the set names of the layers to be displayed on a display, and accepts, in accordance with a user operating input made on the list, an instruction of indicating which one of the layers is to be used to generate the electronic document.

9. The medical image processing apparatus according to claim 2, wherein the surface shape generation unit generates the surface shape data after extracting a region in accordance with a preset condition and setting the extracted region as the layer.

10. The medical image processing apparatus according to claim 2, wherein the control unit performs control to generate the electronic document such that whether to display the electronic document or not is switched over for each of the layers at a terminal at which the electronic document is viewed.

11. The medical image processing apparatus according to claim 1, wherein the electronic document is in PDF format.

12. The medical image processing apparatus according to claim 1, wherein the at least one processor is further configured to operate as an extraction condition management unit that manages an extraction corresponding to analysis software installed in the medical image processing apparatus.

13. The medical image processing apparatus according to claim 1, wherein the at least one processor is further configured to operate as an entry receiving unit that receives entry of comments from a user,
    wherein the control unit performs control to generate the electronic document such that the electronic document contains the comments received by the entry receiving unit.

14. The medical image processing apparatus according to claim 13, wherein the comments are comments regarding remarks obtained by observing the medical image data, and the electronic document is an image reading report containing the comments regarding the remarks.

15. A medical image processing apparatus of generating an electronic document used to display a three-dimensional body organ model, the medical image processing apparatus comprising:
    a memory storing instructions; and
    at least one processor that, upon execution of the instructions, is configured to operate as:
        an accepting unit that accepts an instruction for generating an electronic document;
    a surface shape generation unit that generates surface shape data from medical image data and stores the surface shape data in a storage; and
    a control unit that generates the electronic document with the three-dimensional body organ model using the surface shape data generated by the surface shape generation unit, in response to the instruction accepted by the accepting unit,
wherein the surface shape generation unit converts the medical image data to the surface shape data in accordance with Marching cubes algorithm, and
wherein the control unit generates the three-dimensional body organ model divided into a plurality of layers.

* * * * *